(12) United States Patent
Lennon-Meyer et al.

(10) Patent No.: US 11,874,060 B2
(45) Date of Patent: Jan. 16, 2024

(54) CONTINUOUS THROUGHPUT LYOPHILIZER-POWDER FILLER WITHIN A STERILE BOUNDARY

(71) Applicant: Sublime Stericeuticals Corporation, Fort Dodge, IA (US)

(72) Inventors: Joel Peter Lennon-Meyer, Fort Dodge, IA (US); Shawn Anthony Stimson, Saint Joseph, IL (US)

(73) Assignee: Sublime Stericeuticals Corporation, Fort Dodge, IA (US)

( * ) Notice: Subject to any disclaimer, the term of this patent is extended or adjusted under 35 U.S.C. 154(b) by 0 days.

(21) Appl. No.: 18/037,246

(22) PCT Filed: Nov. 16, 2021

(86) PCT No.: PCT/US2021/059544
§ 371 (c)(1),
(2) Date: May 16, 2023

(87) PCT Pub. No.: WO2022/104274
PCT Pub. Date: May 19, 2022

(65) Prior Publication Data
US 2023/0324118 A1    Oct. 12, 2023

Related U.S. Application Data

(60) Provisional application No. 63/114,211, filed on Nov. 16, 2020.

(51) Int. Cl.
*F26B 5/06*    (2006.01)
*F26B 11/04*    (2006.01)
(Continued)

(52) U.S. Cl.
CPC .................. *F26B 5/06* (2013.01); *A61K 9/19* (2013.01); *F26B 11/028* (2013.01); *F26B 11/04* (2013.01)

(58) Field of Classification Search
CPC .......... F26B 5/06; F26B 11/028; F26B 11/04; A61K 9/19
See application file for complete search history.

(56) References Cited

U.S. PATENT DOCUMENTS 1,080,629 A * 12/1913 Griswold et al. ......... F26B 5/06
34/605
2,411,152 A * 11/1946 Folsom ..................... F26B 5/06
264/5

(Continued)

FOREIGN PATENT DOCUMENTS

CN        105000577 A    10/2015

OTHER PUBLICATIONS

International Searching Authority, "International Search Report and Written Opinion," issued in connection with PCT/US2021/059544, dated Feb. 4, 2022, 10 pages.

*Primary Examiner* — Edelmira Bosques
*Assistant Examiner* — Bao D Nguyen
(74) *Attorney, Agent, or Firm* — Nyemaster Goode, P.C.

(57) ABSTRACT

A continuous feed lyophilizer drying chamber that has an overall internal volume, a primly drying stage portion having a primary drying stage internal volume, a secondary drying stage portion having an internal volume, a frozen formulation feed inlet that provides frozen formulation droplets into the internal volume of the primary drying stage of the drying chamber and a dried particle outlet proximate an end of the continuous feed lyophilizer drying chamber configured to provide dried formulation droplet particles. The primary drying stage typically makes up from about 65-75% of the overall internal volume of the drying chamber and the secondary drying stage makes up from 25 to 35% of the overall internal volume of the drying chamber. The drying chamber dries frozen formulation droplets received (Continued)

into the primary drying stage internal volume via the frozen formulation feed inlet.

20 Claims, 5 Drawing Sheets

(51) Int. Cl.
    *F26B 11/02*     (2006.01)
    *A61K 9/19*     (2006.01)

(56) References Cited

U.S. PATENT DOCUMENTS

| | | | | |
|---|---|---|---|---|
| 2,552,360 | A * | 5/1951 | Zichis | F26B 5/06 241/97 |
| 2,616,604 | A * | 11/1952 | Folsom | B01D 7/00 53/484 |
| 2,751,687 | A * | 6/1956 | Colton | B01J 2/00 264/28 |
| 3,024,117 | A * | 3/1962 | Barlow | F25C 1/00 62/57 |
| 3,088,222 | A * | 5/1963 | Mace | F26B 5/06 34/92 |
| 3,264,747 | A * | 8/1966 | Fuentevilla | F26B 3/34 219/679 |
| 3,266,169 | A * | 8/1966 | Smith, Jr. | F26B 5/06 62/347 |
| 3,270,432 | A * | 9/1966 | Barbareschi | B01D 7/00 34/305 |
| 3,290,788 | A * | 12/1966 | Seelandt | F26B 5/065 34/294 |
| 3,303,578 | A * | 2/1967 | Rockwell | F26B 5/06 34/142 |
| 3,324,565 | A * | 6/1967 | Smith, Jr. | F26B 5/06 34/92 |
| 3,362,835 | A * | 1/1968 | Thuse | A23F 5/32 159/4.06 |
| 3,574,951 | A * | 4/1971 | Oetjen | F26B 17/26 34/92 |
| 3,648,379 | A * | 3/1972 | Mercer | A23F 5/32 34/92 |
| 3,677,405 | A * | 7/1972 | Keith, Jr. | C02F 11/20 210/197 |
| 3,740,860 | A * | 6/1973 | Smith, Jr. | F26B 5/06 34/92 |
| 4,748,817 | A * | 6/1988 | Oura | F25C 1/00 417/151 |
| 7,836,606 | B2 * | 11/2010 | Gehrmann | F26B 5/065 34/284 |
| 8,012,313 | B2 * | 9/2011 | Carson | B01D 9/0027 426/384 |
| 8,322,046 | B2 * | 12/2012 | Wang | F26B 5/065 34/286 |
| 8,337,895 | B2 * | 12/2012 | Bennett | A61K 9/0075 424/489 |
| 8,533,972 | B2 * | 9/2013 | Hubbard, Jr. | B01J 2/04 110/235 |
| 8,978,268 | B2 * | 3/2015 | Itou | F26B 5/065 34/291 |
| 9,347,707 | B2 * | 5/2016 | Struschka | F26B 25/16 |
| 9,863,700 | B2 * | 1/2018 | Pedersen | F26B 5/06 |
| 9,945,611 | B2 * | 4/2018 | DeMarco | F26B 5/065 |
| 10,006,706 | B2 | 6/2018 | Luy et al. | |
| 10,436,493 | B2 * | 10/2019 | Wu | B01J 2/04 |
| 11,112,176 | B2 * | 9/2021 | Nishihashi | F26B 5/065 |
| 2003/0186271 | A1 | 10/2003 | Hwang et al. | |
| 2004/0009230 | A1 | 1/2004 | Richard | B01D 33/48 424/489 |
| 2004/0043042 | A1 * | 3/2004 | Johnson | F26B 5/06 34/286 |
| 2004/0154317 | A1 * | 8/2004 | Shekunov | A61K 9/1694 34/285 |
| 2005/0160615 | A1 * | 7/2005 | Wang | B01D 1/18 34/92 |
| 2008/0142166 | A1 * | 6/2008 | Carson | B01D 1/18 159/7 |
| 2008/0155853 | A1 * | 7/2008 | Wang | F26B 5/065 34/286 |
| 2010/0297214 | A1 * | 11/2010 | Haas | A61K 9/1682 34/287 |
| 2011/0016742 | A1 * | 1/2011 | Anderson | F26B 5/065 34/92 |
| 2014/0245629 | A1 | 9/2014 | Luy et al. | |
| 2014/0373383 | A1 * | 12/2014 | Struschka | F26B 5/065 34/92 |
| 2015/0226478 | A1 * | 8/2015 | DeMarco | F26B 5/065 34/92 |
| 2017/0259185 | A1 * | 9/2017 | Madsen | B05B 17/00 |

\* cited by examiner

CONTINUOUS THROUGHPUT LYOPHILIZER-POWDER FILLER WITHIN A STERILE BOUNDARY

CROSS-REFERENCE TO RELATED APPLICATION

This application is a United States National Stage Entry of International Application No. PCT/US21/59544 filed on Nov. 16, 2021, entitled "CONTINUOUS THROUGHPUT LYOPHILIZER/POWDER FILLER WITHIN A STERILE BOUNDARY", which is hereby incorporated by reference in its entirety. International Application No. PCT/US21/59544, entitled "CONTINUOUS THROUGHPUT LYOPHILIZER/POWDER FILLER WITHIN A STERILE BOUNDARY"claims priority to and benefit from U.S. Provisional Application No. 63/114,211, filed on Nov. 16, 2020, entitled "CONTINUOUS THROUGHPUT LYOPHILIZER-POWDER FILLER WITHIN A STERILE BOUNDARY," the disclosure of which is hereby incorporated herein by reference in its entirety.

BACKGROUND

The present disclosure is generally directed toward a lyophilizer system for producing pharmaceutical particles. Lyophilization is a process in which water is removed from a product after it is frozen, which allows the ice to change directly from a solid to vapor without passing through a liquid phase. Generally speaking the process often includes the steps of: freezing, sublimation and desorption. Traditionally, lyophilization systems are certainly not a continuous feed or continuous throughput system. Instead, such systems first fill individual sterile containers that are partially stoppered under aseptic conditions. Next, the vials are transported to a lyophilizer and loaded into a shelved freeze-drying chamber under aseptic conditions. The solutions are then frozen by placing the partially stoppered containers on the cooled shelves in a freeze-drying chamber or pre-freezing in another chamber. Thereafter, a vacuum is applied to the chamber and the shelves are heated in order to sublimate and desorb the water from the frozen state. Finally, the vials are completely stoppered usually by hydraulic or screw rod stoppering mechanisms installed in the lyophilizers. While this process does have some advantages such as enhanced stability of the resultant dry powder and removal of water without excessive heating of the product, traditional lyophilization has significant challenges and difficulties. Traditionally used lyophilization processes require significant handling and processing time because the process is a staged process and not continuous. Additionally, the traditionally used systems are very large and require very complex and expensive equipment.

SUMMARY

One aspect of the present invention includes a continuous feed lyophilizer drying chamber that includes an overall internal volume, a primary drying stage portion having a primary drying stage internal volume, a secondary drying stage portion having an internal volume, a frozen formulation feed inlet that provides frozen formulation droplets into the internal volume of the primary drying stage of the drying chamber and a dried particle outlet proximate an end of the continuous feed lyophilizer drying chamber configured to provide dried formulation droplet particles. The primary drying stage typically makes up from about 65-75% of the overall internal volume of the drying chamber and the secondary drying stage comprises from about 25 to 35% of the overall internal volume of the drying chamber. The drying chamber is configured to dry the frozen formulation droplets received into the primary drying stage internal volume via the frozen formulation feed inlet.

Another aspect of the present invention includes a sterile and continuous flow formulation lyophilization drying system that includes: a spray freezing chamber, a formulation supply system, and a continuous feed lyophilizer drying chamber containing a recirculating system. The formulation system is typically configured to provide a pharmaceutical or biological active containing solution, suspension, or emulsion to the spray freezing chamber and the spray freezing chamber forms a plurality frozen droplets of the pharmaceutical or biologically active containing solution, suspension, or emulsion and supplies the plurality frozen droplets of the pharmaceutical or biological active containing solution, suspension, or emulsion to a primary drying stage section of a drying chamber via a sterile conduit and the primary drying stage section delivers at least partially dried frozen droplets of pharmaceutical or biological active to a secondary drying stage section of the drying chamber. The temperature of the primary drying stage section is less than the secondary drying stage section. The system further includes a continuous feed outlet operably connected to the secondary drying stage section of the continuous feed lyophilizer drying chamber that supplies sterile, dried, and frozen pharmaceutical or biological active particles. Pharmaceutical active particles and biological active particles are typically particles that exert a direct physiological effect on an animal, such as a human, who receives the pharmaceutical active or biological active via injection or enteric administration of the pharmaceutical active and/or biological active produced by the systems/processes described herein.

Yet another aspect of the present invention includes an aseptic method of producing a dried pharmaceutical product without interruption that includes the steps of: preparing a formulation solution of a plurality of components and water; supplying the formulation solution to a spray freezing chamber; freezing the formulation solution in the spray freezing chamber to form frozen droplets; delivering the frozen droplets into a primary drying stage of a rotating drying chamber of a recirculating drying system; and drying the frozen droplets by passing the frozen droplets through the primary drying stage of the rotating drying chamber and into and through a secondary drying stage of the rotating drying chamber to form dried particles from the frozen droplets.

These and other aspects, objects, and features of the present invention will be understood and appreciated by those skilled in the art upon studying the following specification, claims, and appended drawings.

DETAILED DESCRIPTION OF EMBODIMENTS

Figure 1:
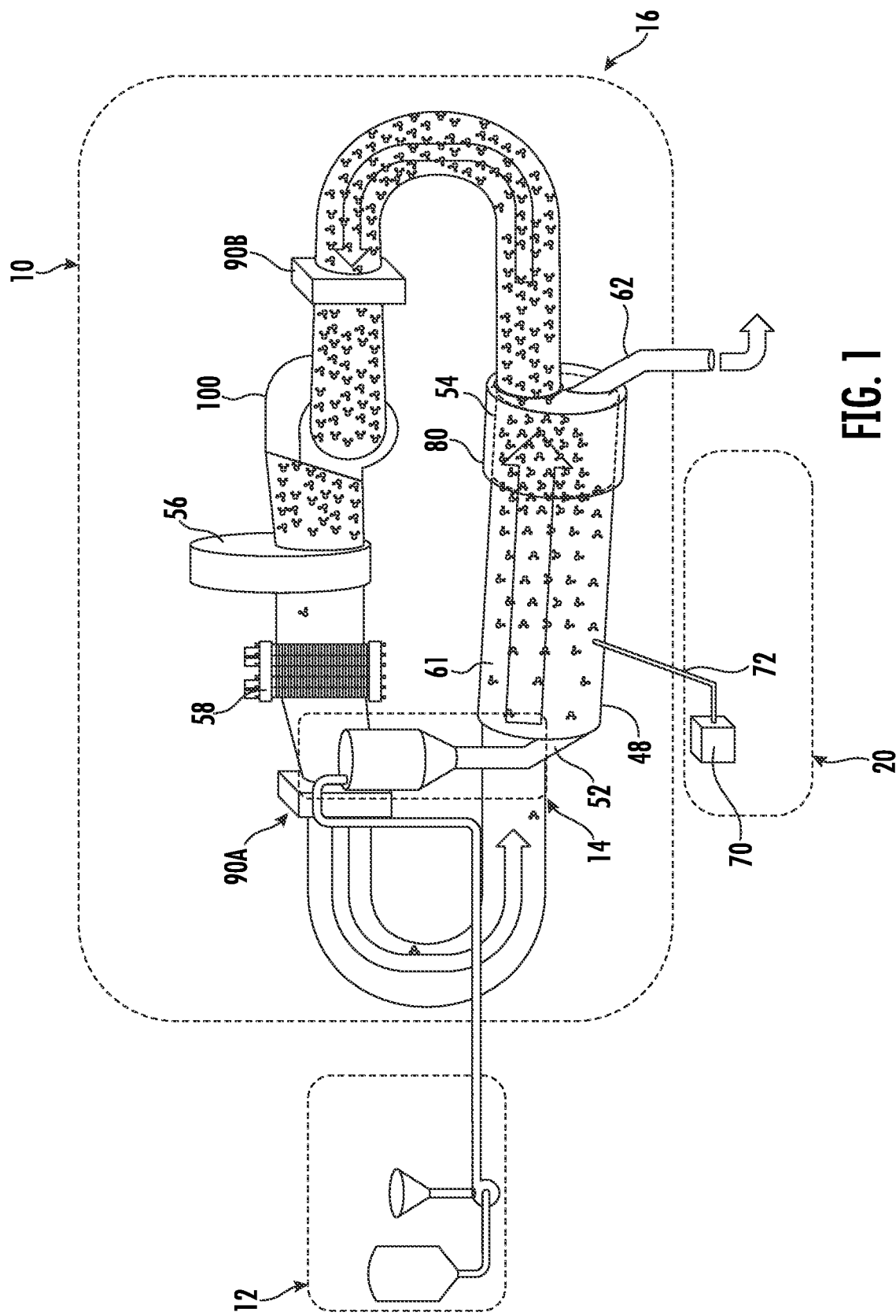
FIG. 1 is a schematic view of an overall atmospheric drying chamber system shown operatively connected with a formulation system, a spray freezing chamber, an ancillary cooling and heating systems, and filler system according to an aspect of the present disclosure.

For purposes of description herein, the terms "upper," "lower," "right," "left," "rear," "front," "vertical," "horizontal," and derivatives thereof shall relate to the invention as oriented in FIG. 1. However, it is to be understood that the invention may assume various alternative orientations, except where expressly specified to the contrary. It is also to be understood that the specific devices and processes illustrated in the attached drawings, and described in the following specification are simply exemplary embodiments of the inventive concepts defined in the appended claims. Hence, specific dimensions and other physical characteristics relating to the embodiments disclosed herein are not to be considered as limiting, unless the claims expressly state otherwise.

All ranges and parameters, including but not limited to percentages, parts, and ratios, disclosed herein are understood to encompass any and all sub-ranges assumed and subsumed therein, and every number between the endpoints. For example, a stated range of "1 to 10" should be considered to include any and all sub-ranges beginning with a minimum value of 1 or more and ending with a maximum value of 10 or less (e.g., 1 to 6.1, or 2.3 to 9.4), and to each integer (1, 2, 3, 4, 5, 6, 7, 8, 9, 10) contained within the range. In this specification and the appended claims, the singular forms "a," "an" and "the" include plural reference unless the context clearly dictates otherwise. All combinations of method steps or process steps as used herein can be performed in any order, unless otherwise specified or clearly implied to the contrary by the context in which the referenced combination is made.

Referring to FIG. 1, reference numeral 10 generally designates a lyophilizer system that may also be used in conjunction with a powder filler. If used in conjunction with a powder filler or not, all processing is typically done within a sterile, closed system framework.

The present disclosure is generally directed toward a continuous throughput lyophilizer/powder filler within a sterile boundary as a closed system and methods of filling a plurality of sterile vials with lyophilized/freeze dried powder filler material. The systems and methods of the present disclosure are typically sterile systems as opposed to simply an aseptic system/method in that the systems of the present disclosure are typically devoid of life. A continuous production system typically involves a continuous or almost continuous physical flow of materials. The systems include a spray-freezing system contained in an insulated chamber with a conical lower portion serving to collect and transfer the frozen particles to a drying chamber. Overall, the drying chamber is essentially a nearly horizontal, thermally jacketed, rotating cylinder. The drying chamber typically includes internal fins or internal surface grooves or other mechanical system to move material as the drying chamber rotates. The fins or internal surface grooves are not absolutely necessary but are present to assist in slowly tumbling the frozen particles as they progress down the slight slope of the cylinder. The fins may be any shape/configuration and may be made of any material, but are typically made of a sterilizable metal and shaped as planar material or corrugated material. The drying chamber typically has at least two stages. The initial stage, which is typically a primary drying stage, makes up about 70% of the cylinder length. This primary drying stage will have its portion of the thermal jacket cooled to around from about −5° C. to about −40° C. During the processes of the present disclosure the material being dried will typically reside within the primary drying stage for from about two to about sixteen (16) hours, more typically six to twelve (12) hours or six to sixteen (16) hours as it progresses via gravity and mechanical motion of the drying chamber from the inlet to the beginning of the secondary drying stage at a rate equivalent to about 500 to about 2500 grams per hour of finished dried powder. Upon completion of primary drying, the water content of the product will be diminished from about 75 to about 95% moisture to about 6% moisture or less. The maximum solids would typically be about 25 percent by weight of the processed material, but would be formulation dependent or output characteristic dependent.

The secondary drying stage will typically make up the remaining about 30% of the cylinder length and will drive off remaining water to levels below 2% or below 1% moisture. The secondary drying stage's typical in-process product retention time is from less than one hour to from about 2.5 hours to 5 hours. The time period in the secondary drying stage is typically about 25% to about 35% of the time period the composition is in the overall drying process, more typically about 30% or exactly 30% of the time in the overall drying time. The secondary drying stage will typically have its portion of the jacket 80 temperature controlled between around 40° C. to −5° C. Pressure and air movement within both stages of the drying chamber will also be controlled. Two pressure/air movement conditions are regulated in a manner to force sublimation. First, the chamber may have a vacuum drawn as low as about 50 microns of mercury (vacuum lyophilization). Second, the chamber may have circulation of a constant source of ultra-dry nitrogen (atmospheric lyophilization). Typically, in the context of the present disclosure, an atmospheric lyophilization process will be used. Ancillary equipment in the vacuum drying case may consist of a vacuum pump and a two-condenser system for condensing ice alternately. In the vacuum drying lyophilization process, the ancillary systems would typically be used to move and condense the vapor. Two or more cooling condensers are typically used so that one can be defrosting while the other is in use. In the atmospheric drying case, the condenser system will be replaced with a more suitable and efficient ancillary water vapor removal system that will typically include a recirculating loop of cold, ultra-dry nitrogen gas driven by blowers, which would typically provide an airflow rate of from about 0.15 m/s to about 0.8 m/s, more typically from about 0.2 m/s to about 0.4 m/s, and more typically about 0.3 m/s through the system, with a desiccant wheel, which is more typically used. The drying chamber's temperature parameters, product retention times, and pressures/air movement will be product dependent. The dried powder exits the chamber and is conveyed to the isolator-contained, accurate and precise, sterile powder dosing system for vial filling. Typically, the dried products have the following physical characteristics: particle size of from about 100 to about 500 micrometers; a residual moisture content of from about 0.5% to about 5%; a sphere-like particle morphology; a bulk powder density of from about 0.4 to about 0.8 g/mL, sterility; and, in the case of mannitol, a reconstitution time of less than about 15 seconds. It should be understood that reconstitution time is highly dependent on whether the process of the present disclosure is properly followed and the specific pharmaceutical formulation or biological active containing formulation. The resultant lyophilized pharmaceutical produced by the process and systems of the present disclosure will also have the same or improved pharmaceutical activity. Typically, the processing will not affect pharmacological activity and/or product stability.

There are a variety of significant advantages to using the systems and processes of the present disclosure over prior lyophilizing processes. The processes and systems of the present disclosure maintain an absolutely sterile boundary surrounding the entire lyophilization and filling process, which results in a significantly decreased chance of foreign biological contamination and in most instances the very low chance of biological contamination is a complete avoidance of biological contamination during the entire process. Perhaps more significantly, since the systems of the present disclosure enable a continuous process, it is presently believed that the systems and process have a greater than ten times throughput capacity over earlier systems. Material may be processed at a rate of at least about one kilogram of freeze-dried powder per hour of operation. Moreover, from about 40% to about 70% less energy is used in the processes/systems of the present disclosure. Finally, the overall monetary costs of the systems of the present disclosure are less than about 40% of a conventional shelf or tray type lyophilizer, which do not permit a continuous batch processing.

As discussed above, a schematic of a lyophilizer/powder filler within a sterile boundary system 10 of the present disclosure is generally shown in FIG. 1. The atmospheric drying chamber system of the present disclosure is typically a continuous recirculating dry gas feed system. The system includes a formulation stage 12 (See FIGS. 1 and 2), a spray freezing frozen droplet forming apparatus 14 (FIGS. 1 and 3), which may be a spray freezing chamber or potentially any other conduit, vessel or housing that has a spray of droplets of drug formulation that collide with liquid nitrogen or other freezing composition to freeze the drug formulation into droplets, a main atmospheric drying chamber 16 (FIGS. 1 and 4), ancillary systems 20 (FIG. 1); and an isolated filling and transfer station (FIG. 5). The ancillary systems 20 can include one or more cooling systems 70 in fluid connection with the drying chamber, typically the primary drying section of the drying chamber, and/or one or more refrigeration or heating subsystem that is in fluid connection with the secondary drying portion of the drying chamber. The one or more cooling systems may be a mechanical refrigeration system, which would typically be the most energy efficient for the temperature needed at this stage of the drying chamber, but could be an alternative cooling system such as a liquid nitrogen cooling system. The system may also be an electric thermal jacket to cool the section of the drying chamber. The system(s) help(s) maintain the correct temperature of the different portions of the drying chamber and allows for regulation of each independently.

Figure 2:
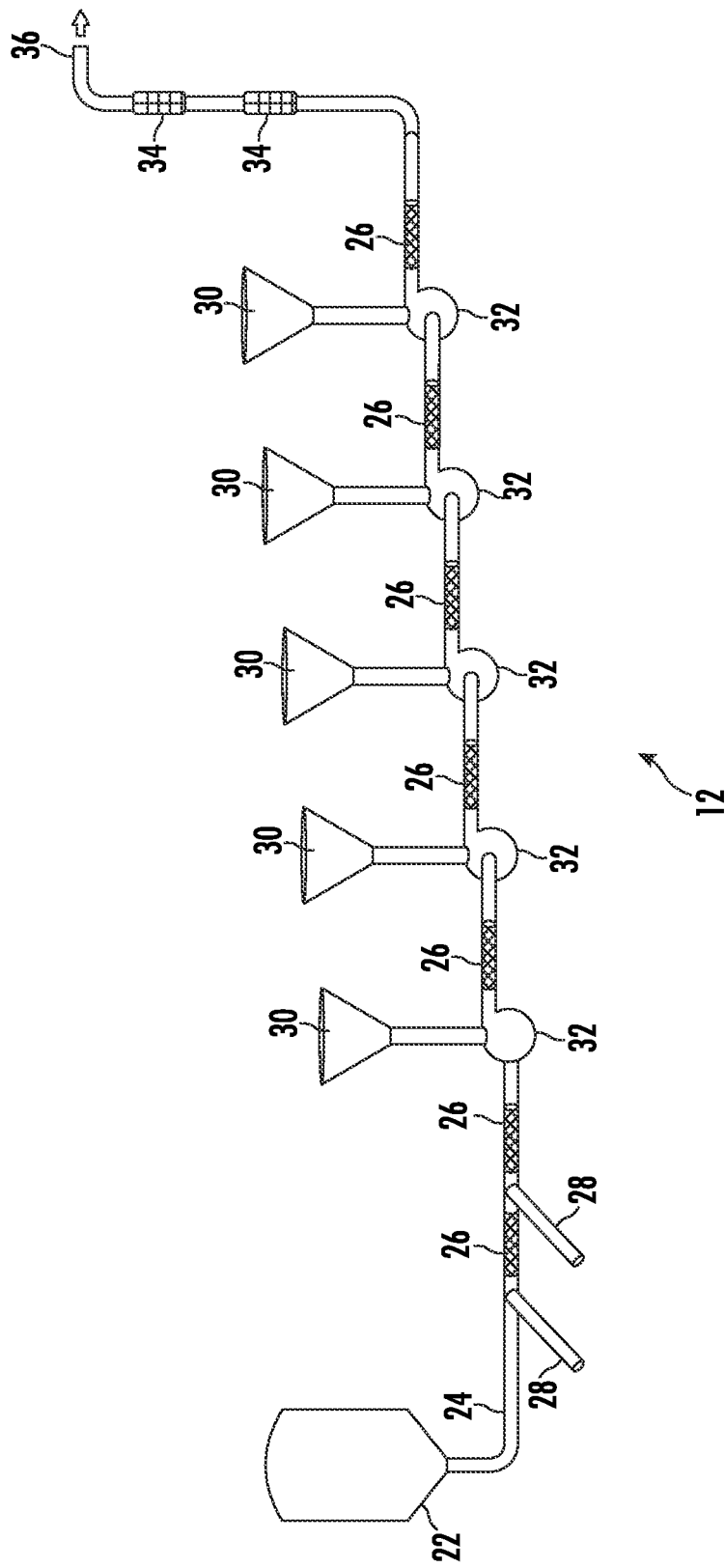
FIG. 2 is a schematic view of a continuous formulation system according to an aspect of the present disclosure.

As shown in FIGS. 1 and 2, a formulation stage of equipment that is a continuous process done before the material is added to the atmospheric drying chamber may be utilized. In the formulation stage shown in greater detail in FIG. 2, the formulation stage of the drug-containing solution will be a continuous process. A solvent tank 22 will contain predominantly water-for-injection (WFI) that will be moved through the formulation system at a measured flow rate (typically at a rate of about 3-6 L/hr., more typically from about 3.5 to about 4.5 L/hr., and more typically about 4.0 L/hr.), but may contain other solvent(s) such as ethanol or other alcohol that may be driven off by the processes of the present disclosure. Typically, the solvent tank 22 contains solely water. Other liquid ingredients such as one or a plurality of liquid drug substances, surfactants, preservatives and/or alcohols may be metered in downstream and as the formula being created passed through one or a series of inline static mixers 26 while traveling through a series of conduits or pipes 24 connecting the solvent tank with the spray freeze dryer. Drug substance(s) and other excipients in the solid state may be added through a series of metered dose, dust-free and loss-free powder induction stations 30 that are in communication with the conduits via a junction 32 and passed through the inline static mixers 26. Typically, one ingredient or a single pre-blend of material will be added per metered dose, dust-free and loss-free powder induction stations 30. Additional static mixers may be added to aid in mixing any hard to dissolve ingredients. Typically, at least one inline static mixer is employed after each ingredient or pre-blend of material is added and before another ingredient or preblended material is added as shown in FIG. 2. A redundant sterilizing-grade filtration system which contains at least two sterilization grade filters 34 will filter the solution as it enters the spray freezing chamber via outlet 36. The entire formulation system 12 will be capable of being cleaned-in-place (CIP) between runs of differing products. Metering capabilities for all ingredients are typically controlled through one or more programable logic controller or other suitable controlling device according to an aspect of the present disclosure. The solutions may be heated or cooled during the formulation process at the same temperature throughout the process or conceivably at different temperatures at different stages through the continuous formulation process. The formulations are typically in the form of a solution, but could conceivably be in the form of a suspension or emulsion with an adjustment of the sterilization filters. The sterilization filters typically contain validated size-exclusion sterile filtration membranes which typically contain submicron-sized pores ($\leq 0.22$ μm) to reproducibly remove viable microorganisms from the process stream, producing a sterile effluent, but could conceivably be a sterilization system that does not solely rely on particle filtration in order to accommodate a suspension or emulsion in the context of the continuous systems of the present disclosure. Typically, the formulation process takes from about 25-35 minutes, but more typically about 30 minutes or less to accomplish. Additionally, the formulations typically contain about 25% dissolved solids or less. The formulation process is typically done under atmospheric pressure.

Figure 3:
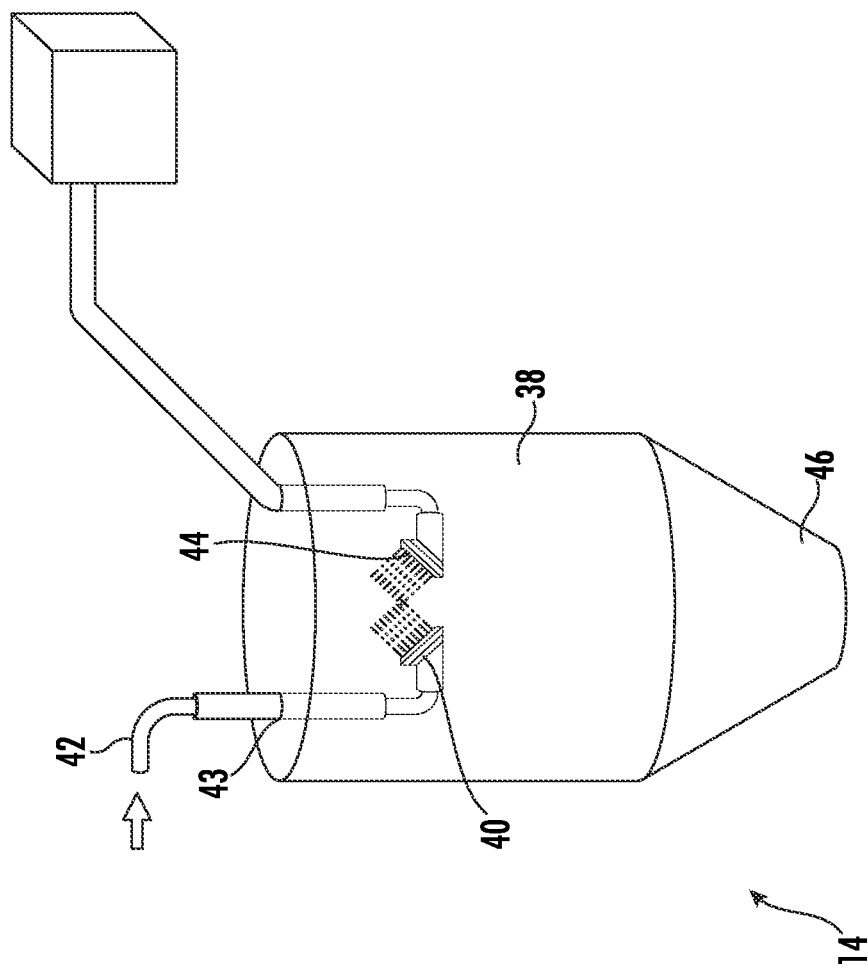
FIG. 3 is a schematic view of a spray freezing chamber according to an aspect of the present disclosure.

The spray freezing chamber 14 of the present disclosure is shown in FIGS. 1 and 3. The spray freezing process is also continuous and connected to the formulation output conduit. Liquid nitrogen is sprayed into the freezing vessel 38 for initial chamber cooling. When the chamber reaches the set temperature or below, the formulated solution is introduced at a measured and controlled flow rate through a spray nozzle 40 via a thermally jacketed solution piping segment 43. The liquid nitrogen spray head 44 and the spray nozzle 40 are typically positioned such that each separate liquid stream exiting each spray head collide with one another, typically at an upward angle, but conceivably directly at one another opposite one another or at a downward angle. The upward angle of the spray heads is presently believed to be advantageous to allow for a longer residence time within the spray freezing frozen droplet forming apparatus 14 and form more universal sized droplets. The droplets have the opportunity to form and have longer residence time before falling to the bottom of the conical portion due to the force of gravity. The air movement within the spray freezing frozen droplet forming apparatus 14 is typically an initially upward archuous pathway and then along and down the sides of the apparatus 14. The spray of the formulated solution from ultrasonic spray nozzle head 40 and from the liquid nitrogen spray head 44 collide and form the frozen droplets with diameters within the target range, which is discussed in more detail below. The frozen droplets are collected through the conical portion 46 at the bottom of the vessel and transported to the drying chamber continuously either via gravity or a cryogenic conveying system, which can be a mechanical system such as an auger system or conceivably a pneumatic system or a combination of one or more systems that could be used collectively alone or also with the force of gravity to convey the frozen droplets to the drying chamber.

As shown in FIG. 3, the formulated solution path is typically thermally jacketed and heated to prevent freezing prior to release as liquid droplets within the freezing chamber; however, it is conceivable that the spray systems may be positioned such that the thermal jacketing is not necessary. The thermal jacketing portion 43 typically extends the entire or substantially all of the distance the conduit of formulated solution travels within the interior of the freezing vessel 38 until reaching the solution spray nozzle head 40. The entire spray-freezing system will be capable of being cleaned-in-place (CIP) and sterilized-in-place (SIP) between runs of differing products. Metering capabilities for the formulated solution in the context of the systems of the present disclosure are typically controlled through one or more programmable logic controllers or another suitable controlling device such as a microcontroller. The spray freezing chamber and the freezing process is typically kept at and undertaken at atmospheric pressure. The liquid nitrogen temperature is typically about −196° C. and the incoming formulated solution temperature is typically at from about 2° C. to about 25° C.; however, higher temperatures may be used and at times prove to be advantageous. The chamber is typically operated at a temperature of less than about −40° C. The frozen formulated solution droplets are typically at a temperature of from about −40° C. to about −90° C. The entire spray freezing process typically has a residence time about 30 seconds or less. The frozen formulation composition is frozen into spherical or nearly spherical frozen droplets with a droplet size of from about 100 to about 500 microns and have a median droplet size of from about 250-300 microns, more typically about 275 microns. The target end material particle size for the frozen droplets is from about 75 microns to about 450 microns.

Figure 4:
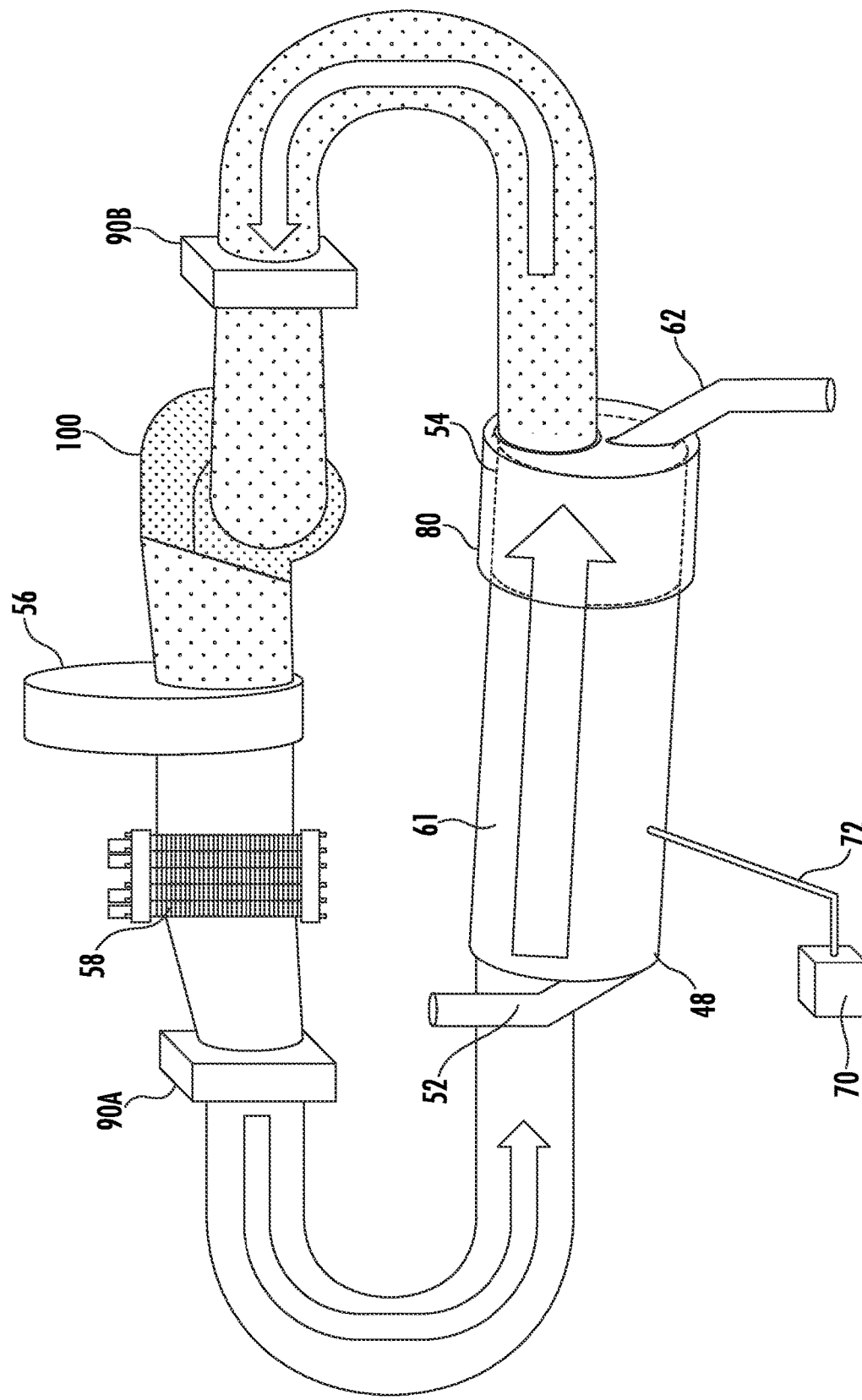
FIG. 4 is a schematic view of the cyclic, continuous closed atmospheric drying chamber containing system.
Figure 5:
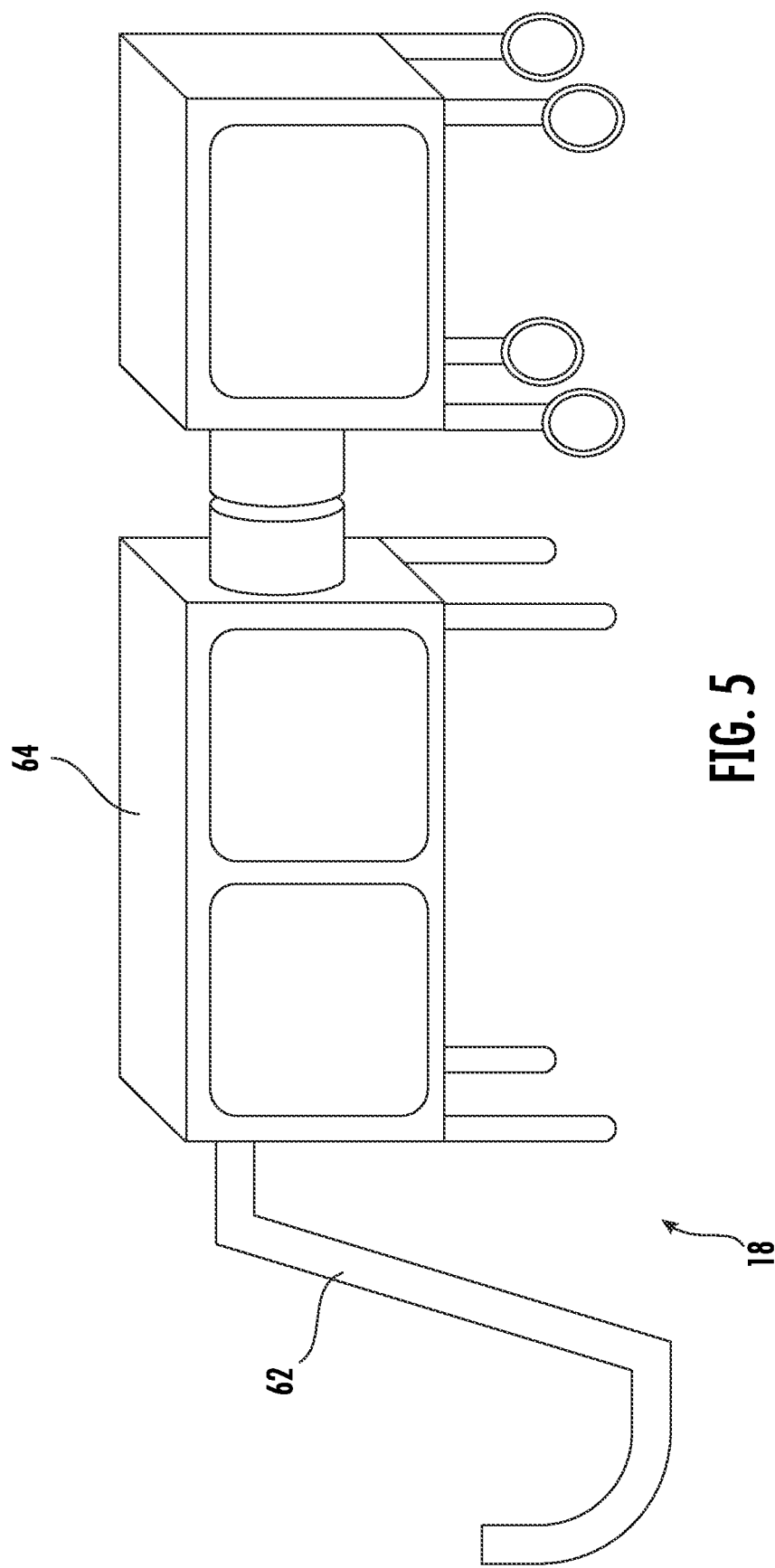
FIG. 5 is a schematic view of a filling isolator and transfer isolator system that may be used in conjunction with the cyclic, continuous closed atmospheric drying chamber.

As shown in FIG. 4, the frozen formulation particles are transferred into the primary stage portion 48 of the drying chamber 50 via the intake conduit 52. As discussed above, there are typically two stages 48, 54 to the atmospheric drying option, which is typically used in the context of the present disclosure. The drying chamber 50 is essentially a nearly horizontal, thermally jacketed, rotating cylinder with internal fins or internal grooves to assist in slowly tumbling the frozen particles as they progress down the slight slope of the cylinder due to the force of gravity and optionally airflow within the system. The fins, when present, are typically metal and are welded or integral with the interior of the rotating cylinder. The fins may be any shape that adequately mixes the contents of the drier. They are often corrugated having alternating ridges and grooves along the surface of fins to create greater mixing. A Munson rotary continuous mixer (or similar mixer) may be adapted to employ a split thermal jacket (not shown in FIG. 4, but present around the rotary mixer) will be used for both primary drying stage 48 and the secondary drying stage 54. The sublimation stage (primary drying) forms approximately the first 65-75%, more typically about the first 70% of the cylinder length and typically will have its portion of the thermal jacket cooled to around −5° C. to −40° C. The in-process residence time in the primary drying stage is from about 2 to 5 hours. The subsequent secondary drying stage 54 typically makes up the remainder of the cylinder length. The particles typically reside in the second stage of the drying chamber for from about 1 to about 2.5 hours. The secondary drying stage will have its portion of the jacket heated or cooled between around 40° C. to −5° C. Incoming frozen droplets coming into the drying chamber typically have a target diameter of from about 5 to about 60 μm. The outgoing dried particles leaving the drying chamber typically have a median diameter within the range of from about 1 to about 20 μm. There will typically be no outer shell for the atmospheric drying chamber. Dry cold air or nitrogen gas will typically flow directly through the chamber from inlet to outlet. Air and/or gaseous nitrogen flow will be in the same direction as product flow. Low velocity airflow or inert gas flow will be supplied through sealed ductwork in a path concurrent with the in-process product flow to enable sublimation and desorption of the drug product. As water molecules are driven out of the frozen droplets, they are transported through the flow of nitrogen gas to a desiccant wheel containing portion 56 of the system, where they are collected and removed from the recirculating gas. The desiccant wheel 56 is typically a sorption dehumidifier using a solid desiccant. The desiccant material is coated, impregnated, or formed in place on the supporting rotor structure. The desiccant wheel is typically a passive desiccant wheel or enthalpy wheel or rotary energy wheel in most embodiments of the present disclosure since there is no regeneration air heater. The desiccant wheel is typically installed with thermal insulation and air-proof material, so no mass and energy exchange take place with the surroundings. The desiccant wheel typically uses a rotary motor to rotate the desiccant wheel in use. Following desiccation, the gas is once again cooled before entering the drying chamber.

In operation, based on product-specific setpoints, immediately prior to a process run the airflow in the atmospheric drying system is started to condition the chamber with ultra-low humidity (typically less than or equal to about 1% RH, but more typically about 0.1% RH or less) nitrogen gas. The typical target supply nitrogen gas temperature measured at the inlet of the drying chamber is typically from about 5° C. to about 15° C. above that of the primary stage thermal jacket while not exceeding the glass transition temperature or collapse temperature of the in-process product. The target supply nitrogen gas flow passes through a heat exchanger 58 to be cooled to the desired temperature. Liquid nitrogen injection may also be used to cool the nitrogen gas. The temperatures of the sublimation portion (the primary drying stage) and desorption portion (the secondary drying stage) of the tumbler are adjusted and controlled. Once the tumbling drying chamber reaches thermal stability and the nitrogen gas temperature is stable at the drying chamber inlet and outlet, the frozen droplets are introduced to the pre-cooled sublimation portion of the tumbler either by gravity or cryogenic conveyance. The frozen droplets progress down the drying chamber via the tumbling action and/or gravity, typically by both actions due to the slightly tilted orientation of the rotating chamber. The frozen droplets transform to drier particles (approximately 5% or less water) along the sublimation portion of the chamber, with further drying through desorption in the secondary drying stage. The fully dried particles, with typical moistures between about 0.5 to about 2%, are continuously discharged and fed via a discharge conduit 62 to the sterile powder filler isolator 64 via gravity or other conveyance (see FIGS. 4 and 5). Additionally, the systems of the present disclosure typically contain one or more high-efficiency particulate air (HEPA) filters. Typically, at least one HEPA filter 90A is employed on the cold side of the system downstream after the heat exchanger on the counterclockwise airflow pathway of the system. A second HEPA filter 90B is typically positioned along the return airflow pathway in advance of an air moving device, which is typically an in-line fan 100. When employed in connection with the systems of the present disclosure, the HEPA filters are filters that are typically capable of removing at least 99.97% of dust, pollen, mold, bacteria, and any airborne particles with a size of 0.3 microns (µm). The diameter specification of 0.3 microns responds to the worst case; the most penetrating particle size (MPPS). Particles that are larger or smaller are trapped with even higher efficiency. Using the worst-case particle size results in the worst-case efficiency rating (i.e. 99.97% or better for all particle sizes).

Also, a particle filter (not shown in the figures) may be present before the return HEPA filter 90B to trap extraneous product microparticles that may be inadvertently transferred via airflow through the drying chamber. This particle filter may be used to preserve the efficiency of the return HEPA filter 90B and/or for reclamation of extraneous product microparticles. The particle filter may be a metal mechanical filter that traps the extraneous product microparticles. The extraneous product microparticles could be re-processed through the system of the present disclosure in the formulation stage or if the extraneous product microparticles meet product specification and are kept sterile, the particles may be combined with the dried particles produced by the system of the present disclosure and sold together when appropriate to do so. The sterile powder fillers that may be utilized in the context of the present disclosure are typically those sold by M&O Perry Industries, which has a place of business at 412 N. Smith Avenue, Corona, California. Such powder fill systems may be powder filling and closing machines for vials/bottles. Indeed, a volumetric filling approach is accurate and repeatable and a filling wheel is typically used to dispense a precise dose of the dried sterile powder and insert stoppers into glass vials at production rates up to 19,200 per hour using certain systems. Low to medium speed powder filling and closing machines may be used at an output of up to 90 cpm (containers per minute) (5,400 cph). Higher speed systems may also be used with an output of up to 300 cpm (18,000 cph) with container sized of from 2R-50H while delivering accurate repeatable and clean dosing as well. High speed macrodose powder filling and closing machines may also be used with continuous motion, minimal powder dust in the machine and an output of up to about 300 cpm (18,000 cph). All powder filling system of the present disclosure typically handle a variety of sizes and shapes of containers including round, oval and square containers.

Following a production run, the drying chamber will be subjected to a manual or automated clean-in-place (CIP) and sterilization-in-place (SIP). Cleaning-In-Place (CIP) and Sterilization-In-Place (SIP) are systems designed for cleaning and sterilizing without major disassembly and assembly work, more typically without any disassembly and assembly work needed. In the case of clean-in-place systems, the systems typically provide the ability to clean the interior surfaces of pipes, vessels, process equipment, filters and associated fittings, without disassembly. The cleaning may be automatically done or upon user input. Cleaning using CIP is faster, less labor-intensive and more repeatable, and poses less of a chemical exposure risk to people. Starting as a manual process, CIP has evolved to include fully automated systems with programmable logic controllers, multiple balance tanks, sensors, valves, heat exchangers, data acquisition and specially designed spray nozzle systems. Subsequent to CIP, SIP can be accomplished through the introduction and maintenance of pressurized clean steam to the equipment to be sterilized in place. Preferred alternatives to sterilization by steam are chemical sterilization using vaporous hydrogen peroxide or gaseous chlorine dioxide, for example.

It will be understood by one having ordinary skill in the art that construction of the described invention and other components is not limited to any specific material. Other exemplary embodiments of the invention disclosed herein may be formed from a wide variety of materials, unless described otherwise herein.

For purposes of this disclosure, the term "coupled" (in all of its forms, couple, coupling, coupled, etc.) generally means the joining of two components (electrical or mechanical) directly or indirectly to one another. Such joining may be stationary in nature or movable in nature. Such joining may be achieved with the two components (electrical or mechanical) and any additional intermediate members being integrally formed as a single unitary body with one another or with the two components. Such joining may be permanent in nature or may be removable or releasable in nature unless otherwise stated.

It is also important to note that the construction and arrangement of the elements of the invention as shown in the exemplary embodiments is illustrative only. Although only a few embodiments of the present innovations have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts or elements shown as multiple parts may be integrally formed, the operation of the interfaces may be reversed or otherwise varied, the length or width of the structures and/or members or connector or other elements of the system may be varied, the nature or number of adjustment positions provided between the elements may be varied. It should be noted that the elements and/or assemblies of the system may be constructed from any of a wide variety of materials that provide sufficient strength or durability, in any of a wide variety of colors, textures, and combinations. Accordingly, all such modifications are intended to be included within the scope of the present innovations. Other substitutions, modifications, changes, and omissions may be made in the design, operating conditions, and arrangement of the desired and other exemplary embodiments without departing from the spirit of the present innovations.

It will be understood that any described processes or steps within described processes may be combined with other disclosed processes or steps to form structures within the scope of the present invention. The exemplary structures and processes disclosed herein are for illustrative purposes and are not to be construed as limiting.

It is also to be understood that variations and modifications can be made on the aforementioned structures and methods without departing from the concepts of the present disclosure, and further it is to be understood that such concepts are intended to be covered by the claims unless the claims by their language expressly state otherwise.

What is claimed is:

1. A continuous feed lyophilizer drying chamber comprising an overall internal volume, a primary drying stage portion having a primary drying stage internal volume, a secondary drying stage portion having an internal volume, a frozen formulation feed inlet that provides frozen formulation droplets into the internal volume of the primary drying stage portion of the continuous feed lyophilizer drying chamber and a dried particle outlet proximate an end of the continuous feed lyophilizer drying chamber configured to provide dried formulation droplet particles and wherein the primary drying stage portion comprises from about 65-75% of the overall internal volume of the continuous feed lyophilizer drying chamber and the secondary drying stage portion comprises from about 25 to about 35% of the overall internal volume of the continuous feed lyophilizer drying chamber and wherein the continuous feed lyophilizer drying chamber dries the frozen formulation droplets received into the primary drying stage internal volume via the frozen formulation feed inlet.

2. The continuous feed lyophilizer drying chamber of claim 1, wherein the continuous feed lyophilizer drying chamber has an interior shape and the interior shape is a right cylinder.

3. The continuous feed lyophilizer drying chamber of claim 1, wherein the primary drying stage portion and the secondary drying stage portion are adjacent one another and undivided from one another.

4. The continuous feed lyophilizer drying chamber of claim 3, wherein the continuous feed lyophilizer drying chamber has an exterior shape of a right cylinder with a primary drying stage base end and a secondary drying stage base end and further comprises a main airflow intake aperture on the primary drying stage base end and a main airflow outlet aperture on the secondary drying stage base end.

5. The continuous feed lyophilizer drying chamber of claim 3 further comprising a main airflow intake aperture proximate one end of the continuous feed lyophilizer drying chamber and proximate an initial portion of the primary drying stage portion and a main airflow outlet aperture proximate an opposite end of the continuous feed lyophilizer drying chamber and proximate an end stage of the secondary drying stage portion.

6. The continuous feed lyophilizer drying chamber of claim 5, wherein the continuous feed lyophilizer drying chamber is a cylindrically-shaped drying chamber and the main airflow intake aperture proximate the initial portion of the primary drying stage portion is larger than half of a surface area of a first base of the cylindrically-shaped drying chamber and the main airflow outlet aperture is larger than half of a surface area of a second base of the cylindrically-shaped drying chamber.

7. The continuous feed lyophilizer drying chamber of claim 6 further comprising:

a thermal jacketing around an exterior of the continuous feed lyophilizer drying chamber; and a split thermal jacket configured to maintain different temperatures of the primary drying stage portion and the secondary drying stage portion.

8. The continuous feed lyophilizer drying chamber of claim 7, wherein an interior surface of the continuous feed lyophilizer drying chamber further comprises a plurality of internal fins or grooves configured to tumble frozen particles within the primary drying stage internal volume of the primary drying stage portion and the internal volume of the secondary drying stage portion of the continuous feed lyophilizer drying chamber and wherein the continuous feed lyophilizer drying chamber further comprises nitrogen gas within the overall internal volume of the continuous feed lyophilizer drying chamber and having a temperature measured at a nitrogen gas inlet of the continuous feed lyophilizer drying chamber of from about 5° C. to about 15° C. above that of a primary stage thermal jacket while not exceeding a glass transition temperature or collapse temperature of in-process product.

9. The continuous feed lyophilizer drying chamber of claim 8, wherein the plurality of internal fins or grooves are fins and the fins are on an internal surface of the continuous feed lyophilizer drying chamber and the fins are metal and welded or integral with the internal surface of a right cylinder.

10. The continuous feed lyophilizer drying chamber of claim 9, wherein the fins are corrugated and have alternating ridges and grooves along a surface of the fins.

11. The continuous feed lyophilizer drying chamber of claim 10, wherein the primary drying stage portion forms approximately the first 65-75 percent of both a length and the overall internal volume of the continuous feed lyophilizer drying chamber and the secondary drying stage portion constitutes a remaining portion of the continuous feed lyophilizer drying chamber.

12. The continuous feed lyophilizer drying chamber of claim 11, wherein the primary drying stage portion has a thermal jacket portion that maintains the temperature of the primary drying stage portion at a temperature of from about −5° C. to −40° C. and wherein the secondary drying stage portion is immediately subsequent a primary drying chamber and makes up a remainder of the overall volume of the continuous feed lyophilizer drying chamber and wherein the secondary drying stage portion's thermal jacketing maintains the temperature of the secondary drying stage portion at a temperature of from about −5° C. to about 40° C. and wherein the frozen formulation droplets comprise a pharmaceutically active drug or other biological active configured to be intravenously administered to a patient in need thereof.

13. A sterile and continuous flow formulation lyophilization drying system comprising:

a spray freezing chamber, a formulation supply system, and the continuous feed lyophilizer drying chamber of claim 1 further comprising a recirculating system, and wherein the sterile and continuous flow formulation lyophilization drying system is configured to provide a pharmaceutical active or a biological active containing solution, suspension, or emulsion to the spray freezing chamber and the spray freezing chamber forms a plurality frozen droplets of the pharmaceutical active or biologically active containing solution, suspension, or emulsion and supplies the plurality frozen droplets of the pharmaceutical active or biological active containing solution, suspension, or emulsion to the primary drying stage portion of the continuous feed lyophilizer drying chamber via a sterile conduit and the primary drying stage portion delivers at least partially dried frozen droplets of pharmaceutical or biological active to the secondary drying stage portion of the continuous feed lyophilizer drying chamber, wherein the temperature of the primary drying stage portion is less than the temperature of the secondary drying stage portion, wherein the system further comprises a continuous feed outlet operably connected to the secondary drying stage portion of the continuous feed lyophilizer drying chamber that supplies sterile, dried, and frozen pharmaceutical or biological active particles, and wherein the pharmaceutical active or the biological active is a particle that exerts a direct physiological effect on an animal who receives the pharmaceutical active or the biological active via injection or enteric administration of the pharmaceutical active or the biological active.

14. A sterile and continuous flow formulation lyophilization drying system comprising:
a spray freezing chamber,
a formulation supply system, and
a continuous feed lyophilizer drying chamber containing recirculating system, and
wherein the sterile and continuous flow formulation system is configured to provide a pharmaceutical active or a biological active containing solution, suspension, or emulsion to the spray freezing chamber and the spray freezing chamber forms a plurality frozen droplets of the pharmaceutical active or biologically active containing solution, suspension, or emulsion and supplies the plurality frozen droplets of the pharmaceutical active or the biological active containing solution, suspension, or emulsion to a primary drying stage section of the drying chamber via a sterile conduit and the primary drying stage section delivers at least partially dried frozen droplets of pharmaceutical active or biological active to a secondary drying stage section of the drying chamber, and
wherein the temperature of the primary drying stage section is less than the temperature of the secondary drying stage section, and
wherein the system further comprises a continuous feed outlet operably connected to the secondary drying stage section of the drying chamber that supplies sterile, dried, and frozen pharmaceutical or biological active particles.

15. The sterile and continuous flow formulation lyophilization drying system of claim 14, wherein the continuous feed outlet supplied a sterile powder filling station via a sterile conduit system.

16. The sterile and continuous flow formulation lyophilization drying system of claim 15, wherein the plurality of frozen droplets coming into the drying chamber have a diameter of from about 100 to about 500 μm and dried particles leaving the drying chamber have a median diameter within a range of from about 1 to about 20 μm.

17. The sterile and continuous flow formulation lyophilization drying system of claims 14 further comprising an air moving fan system, a desiccant wheel, a heat exchanger, at least one high-efficiency particulate air filter and recirculating conduits that operably connect an air moving fan, the desiccant wheel, the heat exchanger, the at least one high-efficiency particulate air filter and the drying chamber such that a continuous airflow loop is formed where air flows out of the secondary drying stage section of the drying chamber, through the desiccant wheel, the heat exchanger, the at least one high-efficiency particulate air filter and into the primary drying stage section of the drying chamber.

18. The sterile and continuous flow formulation lyophilization drying system of claim 17, wherein the system comprises at least two high efficiency particulate air filters, a supply side filter positioned between the heat exchanger and the drying chamber and a return side filter positions between the drying chamber and the desiccant wheel.

19. The sterile and continuous flow formulation lyophilization drying system of claim 18, wherein the drying chamber comprises an overall internal volume, the primary drying stage section having a primary drying stage internal volume, the secondary drying stage section having a secondary drying stage internal volume, a frozen formulation feed inlet that provides frozen formulation droplets into the primary drying stage internal volume of the primary drying stage section of the drying chamber and a dried particle outlet proximate an end of the continuous feed lyophilizer drying chamber configured to provide dried formulation droplet particles and wherein the primary drying stage section comprises from about 65-75% of the overall internal volume of the drying chamber and the secondary drying stage section comprises from 25 to 35% of the overall internal volume of the drying chamber and wherein the drying chamber is configured to dry the frozen formulation droplets received into the primary drying stage section internal volume via the frozen formulation feed inlet and wherein the drying chamber has an interior shape that is a right cylinder.

20. The sterile and continuous flow formulation lyophilization drying system of claim 19, wherein the primary drying stage section internal volume and the secondary drying stage section internal volume are adjacent one another and undivided from one another.

* * * * *